United States Patent [19]

Johnson et al.

[11] Patent Number: 4,942,297
[45] Date of Patent: Jul. 17, 1990

[54] REAL TIME INFRARED AEROSOL ANALYZER

[75] Inventors: Stanley A. Johnson, Countryside; Gerald T. Reedy, Bourbonnais; Romesh Kumar, Naperville, all of Ill.

[73] Assignee: The United States of America as represented by the United States Department of Energy, Washington, D.C.

[21] Appl. No.: 273,395

[22] Filed: Nov. 18, 1988

[51] Int. Cl.⁵ ............................................. G01N 21/01
[52] U.S. Cl. ..................................... 250/304; 356/38
[58] Field of Search ........................... 250/304; 356/38

[56] References Cited

U.S. PATENT DOCUMENTS 4,570,494  2/1986  Dunn et al. ....................... 73/863.22

OTHER PUBLICATIONS

Johnson et al., Chemical Charact. of Atmosph. Aerosol using ATR IR Spectroscopy, AICHE Symposium Series, (1981).

Primary Examiner—Janice A. Howell
Assistant Examiner—Richard Hanig
Attorney, Agent, or Firm—Mark P. Dvorscak; Robert J. Fisher; William R. Moser

[57] ABSTRACT

Apparatus for analyzing aerosols in essentially real time includes a virtual impactor which separates coarse particles from fine and ultrafine particles in an aerosol sample. The coarse and ultrafine particles are captured in PTFE filters, and the fine particles impact onto an internal light reflection element. The composition and quantity of the particles on the PTFE filter and on the internal reflection element are measured by alternately passing infrared light through the filter and the internal light reflection element, and analyzing the light through infrared spectrophotometry to identify the particles in the sample.

9 Claims, 4 Drawing Sheets

REAL TIME INFRARED AEROSOL ANALYZER

CONTRACTUAL ORIGIN OF THE INVENTION

The United States Government has rights to this invention pursuant to Contract W-31-109-ENG-38 with the United States Department of Energy.

BACKGROUND OF THE INVENTION

This invention relates to aerosol analyzers, and more particularly, to infrared aerosol analyzers which operate and report results in essentially real time, as events actually occur.

Obtaining accurate measurements of the particle and gas content of the earth's atmosphere and other environments is important to monitor and understand such environments, and changes in the environments. It is useful to chemically characterize and quantify particles of various sizes, such as "ultrafine" particles (less than about 0.3 micrometers), "fine" particles (about 0.3-1 micrometers) and "coarse" particles (about 1-10 micrometers) in the environments, and to measure transient events involving, for example, volatile materials or sequential collections of reactive mixtures containing acidic and basic materials. It is also useful to be able to make field adjustments of the measuring equipment during operation.

Accurate measurements of aerosol samples can be obtained by passing a sample across a series of attenuated internal reflection elements which can be moved at a controlled rate. This has been done in aircraft and other field locations. In known apparatus, particles from the aerosol sample which adhere to the reflection elements are taken to a laboratory for spectroscopic analysis which reveals the chemical nature of the particles. In spectroscopic analysis, infrared light is passed through the reflection elements and analyzed by measuring the frequencies of light which are absorbed by the particles. However, such analyses are not made in "real time", i.e., as events occur, and therefore have limited usefulness for research and other purposes. A problem with this is that a significant amount of time passes between the time the samples are taken and the time the results are obtained. Consequently, inaccurate results are obtained if the sample changes because the collected materials interact. Also, artifact species can be formed during this interim time, and temporal variations in the sampled environment can be missed. Moreover, sample preparation and analysis are time consuming and expensive when using these known methods. Thus, there is a need for methods and apparatus for accurately analyzing the content of atmospheric particulate matter or aerosols and the like in essentially real time.

Accordingly, an object of this invention is to provide new and improved methods and apparatus for analyzing aerosols.

Another object is to provide new and improved methods and apparatus for analyzing aerosols in essentially real time.

Yet another object is to provide new and improved methods and apparatus for analyzing aerosols which reveal temporal variations of an aerosol in essentially real time.

Still another object is to provide new and improved methods and apparatus for analyzing aerosols which reduce artifact formation and reactions of particles with gasses and other particles prior to analysis.

SUMMARY OF THE INVENTION

In keeping with one aspect of this invention, apparatus is disclosed for collecting and analyzing fractions of various predetermined size particles in aerosols in essentially real time. The apparatus includes a virtual impactor which separates an aerosol sample into a plurality of fractions each having selected particle sizes. In one embodiment, a coarse particle fraction is separated from fine and ultrafine particle fractions in the aerosol sample. The coarse particle fraction is drawn into a chamber having a filter made of polytetrafluoroethylene ("PTFE") or some other suitable material which is semi-transparent to infrared radiation. The fine particle fraction impacts on one or more internal light reflection elements which collect the fine particles. The ultra-fine particle fraction passes through the impactor chamber and is collected on a second PTFE filter in a second chamber which is similar to the coarse particle collector chamber. The particles in the PTFE filters and internal reflection element are analyzed by alternately passing infrared light through them and measuring the light through spectrophotometry to identify the particles and some gasses in the sample. The apparatus is essentially self-contained, and is portable for use in mobil units or field sites

BRIEF DESCRIPTION OF THE DRAWINGS

The above-mentioned and other features of an embodiment of this invention and the manner of obtaining them will become more apparent, and will be best understood by reference to the following description, taken in conjunction with the accompanying drawings, in which.

DETAILED DESCRIPTION

Figure 1:
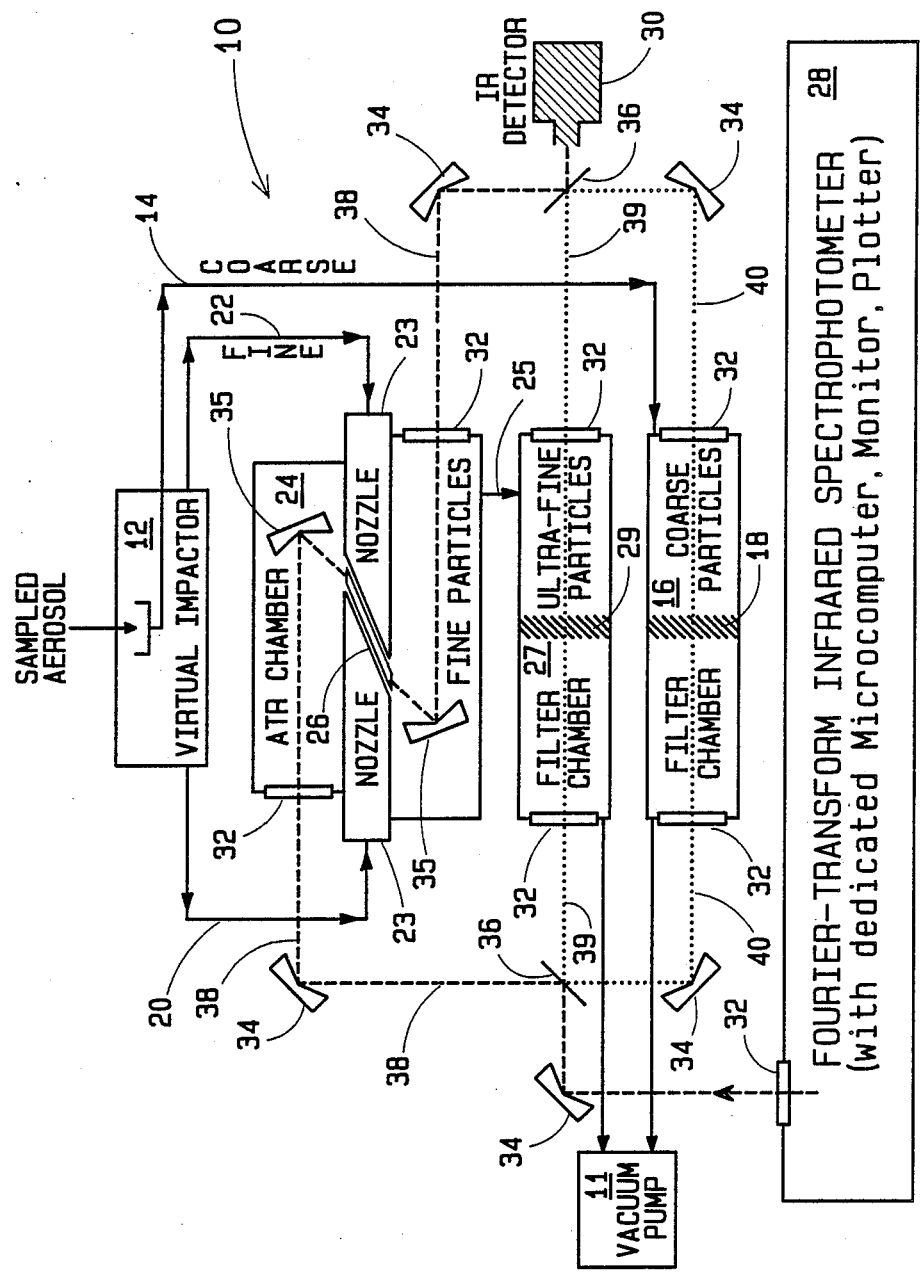
FIG. 1 is a schematic diagram of apparatus made in accordance with the principles of this invention.
Figure 2:
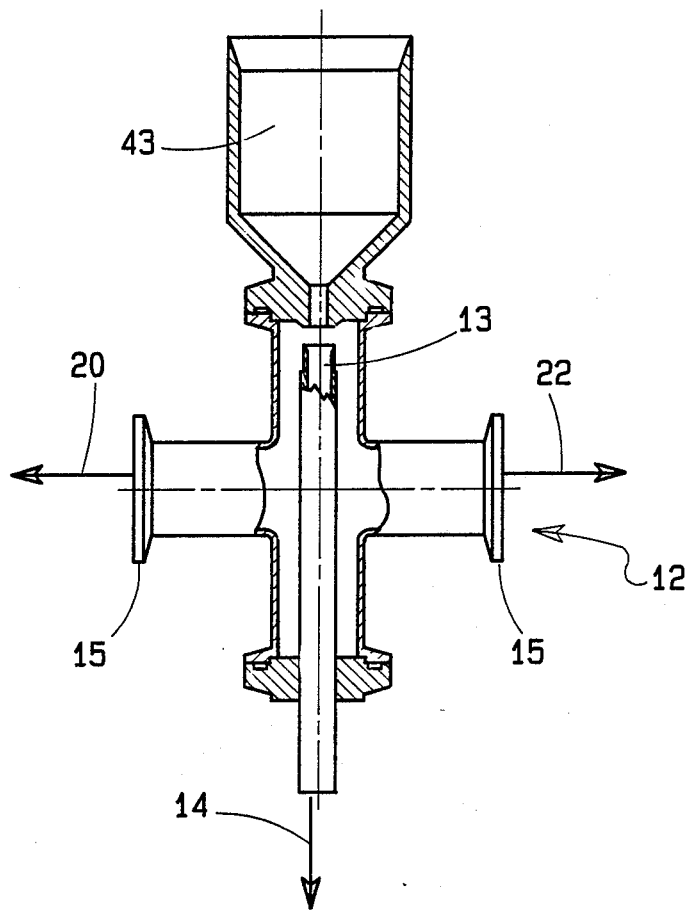
FIG. 2 is a side cross-sectional view of the virtual impactor included in the apparatus of FIG. 1.
Figure 3:
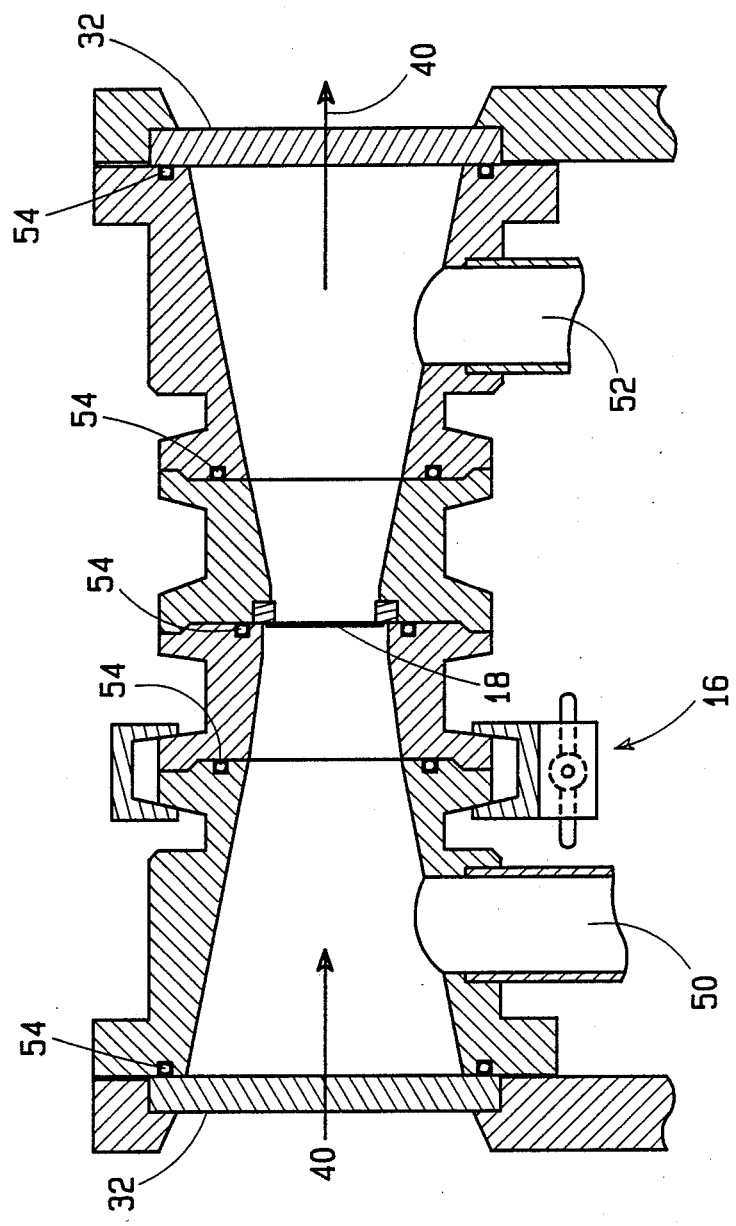
FIG. 3 is a side cross-sectional view of the coarse particle collector included in the apparatus of FIG. 1.

As seen in FIG. 1, apparatus 10 for analyzing aerosol samples includes a virtual impactor 12. An aerosol sample is drawn through the apparatus 10 by a vacuum pump 11.

The impactor 12 separates the aerosol sample into one fraction which includes coarse particles, and another fraction which includes fine and ultrafine particles. For these purposes, particles are considered ultrafine if they are less than about 0.3 micrometers in aerodynamic diameter, fine if they are about 0.3-1 micrometers in aerodynamic diameter, and coarse if they are about 1-10 micrometers in aerodynamic diameter.

The fraction of the sample which includes the coarse particles is routed through a path 14 to a coarse particle collector 16. The collector 16 includes an internal PTFE filter 18.

Figure 4:
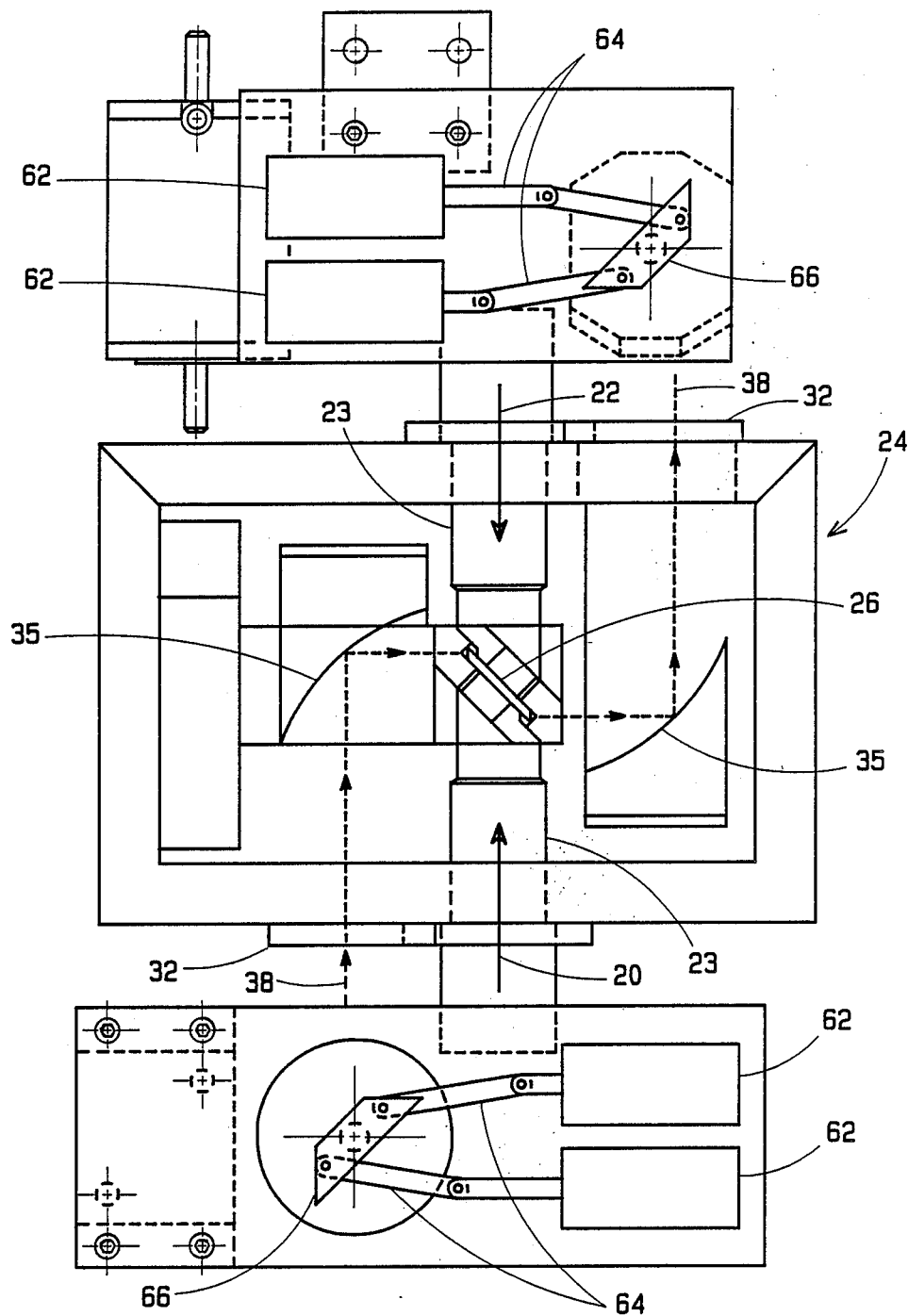
FIG. 4 is a top view of the attenuated total internal reflection ("ATR") impactor chamber and mirror movement mechanism which is included in the apparatus of FIG. 1.

The fraction of the sample which includes the ultrafine and fine particles is split and routed through two paths 20, 22 to two opposing nozzles 23 in an impactor chamber 24. The impactor chamber 24 includes at least one attenuated total internal reflection element 26 ("ATR"), also shown in FIG. 4. In the impactor 24, the gas and particles passing through paths 20, 22 are directed towards the ATR element 26 by the nozzles 23.

The ultrafine particles are separated from the fine particles in the impactor chamber 24. The inertia of the fine particles is sufficient to cause them to impact and adhere to the sides of the reflection element 26, while the ultrafine particles follow the flow of air around the reflection element and out of the impactor 24 through a path 25 to a second filter chamber 27.

The vacuum pump 11 draws the fine/ultrafine size fraction from the ATR impactor 24 to the second filter chamber 27. The filter chamber 27 may be similar to the chamber 16, with a PTFE filter 29, but the filter 29 is capable of capturing the ultrafine particles. The size ranges or "cut points" of the various size fractions can be determined by selecting appropriate impactor nozzle parameters, and additional size fractions can be analyzed as desired by modifying the apparatus 10 to include additional impactor or filter chambers.

A commercially available infrared spectrophotometer 28 emits infrared light which is eventually reflected to an infrared light detector 30, as will be seen. The spectrophotometer 30 could be a Bomen Michelson 100 spectrophotometer or any other suitable device.

The ultrafine collector 27, the coarse particle collector 16 and the impactor 24 include a plurality of windows 32 which pass infrared light without significant reflection or attenuation. The windows 32 can be made of potassium bromide (KBr) or any other suitable infrared transmitting material.

A plurality of mirrors 34 are provided as needed to focus and route the infrared light emitted by the spectrophotometer 28 through the collectors 16 and 27 and the impactor 24 to the detector 30. Parabolic mirrors 35 are provided in the ATR impactor 24 to focus and direct the infrared light through the element 26, as shown in greater detail in FIG. 4.

Movable mirrors 36 are also provided which direct the infrared light alternately through the collector 16, the collector 27 and the impactor 24. In the position shown in FIG. 1, the light passes through the impactor 24 along a path 38. When the mirrors are moved to a substantially horizontal position, the light travels directly through the collector 27 along a path 39, and when the mirrors are rotated further, the light is reflected through the collector 16 along a path 40.

The virtual impactor 12 is shown in greater detail in FIG. 2. A sample from the aerosol environment to be analyzed enters the impactor 12 through an inlet 43. Due to inertial force, the coarse particles follow a relatively straight path through the impactor 12 and exit along the path 14. The fine and ultrafine particles are drawn through two outlet ports 15 along the paths 20, 22. In this manner, the coarse particles are substantially separated from the fine and ultrafine particles.

FIG. 3 shows the collector 16 in greater detail. The fraction of the sample to be analyzed enters the collector 16 at an inlet 50, the gas stream passes through the PTFE filter 18, which collects the particle fraction, and the gas exits through an outlet 52. The light path 40 passes through the windows 32 and the filter 18. A plurality of O-rings 54 are provided as needed to seal the collector 16 from the outside environment. The collector 27 may be constructed in a similar manner.

The opposing nozzles and internal reflection element of the impactor 24 are shown in greater detail in FIG. 4. The impactor 24 includes a pair of inlet nozzles 23 and at least one internal reflection element 26 which acts as a collection substrate for the fine particle fraction. The use of up to about 20 reflection elements is contemplated, however. Multiple reflection elements can move across the nozzles 23 in the plane perpendicular to the view shown in FIG. 4 at any desired rate of speed. Such multiple elements can also be shifted in and out of the collection zone, if desired, or remain stationary. The drive mechanism for the multiple elements can be computer controlled so that the reflection elements can be either automatically or manually sequenced in and out of the collection zone between the nozzles. Fine particles in the gas passing through the nozzles 23 adhere to the multiple reflection elements as the elements pass the nozzles.

The ATR impactor is preferred for collecting the fine particle fraction because fine size particles can be efficiently collected by impaction. In addition, the penetration of infrared light on the surface of the internal reflection element is of the same order of magnitude as the fine particle diameter.

The mirrors 36 (FIG. 3) are controlled by solenoids 62, as shown in FIG. 4. The solenoids 62 move arms 64, which turn plates 66. The plates 66 are secured to the mirrors 36 (not shown in FIG. 4) to direct the mirrors 36 as desired.

Infrared light from the spectrophotometer 28 is focussed by the mirrors 35 and directed through the element 26 at a 45 degree angle to the element, as seen in FIG. 4. The light is reflected internally through the element 26 until it exits through the other end of the element. The element 26 can be any suitable infrared transparent material such as KRS-5, a material made of thallium bromide/thallium iodide. Different materials can be used to meet different needs, such as resistance to acid aerosols.

The fine particles on the outside surfaces of the element 26 which the infrared light strikes as it is internally reflected through the element 26 attenuate certain wavelengths of the light. The attenuated wavelengths are identified when the light is detected by the infrared detector 30 and processed in the spectrophotometer 28. A dedicated microcomputer using commercially available software, with a monitor and plotter (not shown) can be used with the apparatus to process the data obtained.

In use, sampled gas is drawn into the virtual impactor 12, where coarse particles are separated from the fine and ultrafine particles. The sample may be from the atmosphere or any other aerosol source, such as industrial waste, aerosol cans or the like for which analysis is needed. The coarse particles, fine particles and ultrafine particles are analyzed in essentially real time by alternating the positions of the mirrors 36 to direct the infrared light from the spectrophotometer 28 through the collectors 16 and 27, and the impactor 24. It is also contemplated that beam splitters could be used in place of the movable mirrors so that all of the size fractions could be monitored simultaneously. Separate detectors would be needed for each infrared light beam created by the splitters.

The many advantages of this invention are now apparent. Aerosols in the atmosphere can be analyzed in essentially real time, and changes can be monitored as they occur. The chemistry of fine, ultrafine and coarse particles can be easily determined continuously, and the measurements made are accurate and reliable.

While the principles of the invention have been described above in connection with specific apparatus and applications, it is to be understood that this description is made only by way of example and not as a limitation on the scope of the invention.

The embodiments of this invention in which an exclusive property of privilege is claimed are defined as follows:

1. Apparatus for analyzing a sample from an aerosol environment, the sample having gaseous elements with suspended particles, comprising, means for separating the sample into a plurality of size fractions, means for collecting a first fraction in filter means, said collecting means having a first sealed chamber and said filter means being located inside said first chamber, means for impacting a second fraction against an internal reflection element to which said second fraction adheres, said impacting means having a second sealed chamber and said internal reflection element being located inside said second chamber, and means for analyzing said fractions through infrared spectrophotometry in essentially real time, without removing said filter means from said first chamber, or said internal reflection element from said second chamber, said analyzing means including means for emitting infrared light, means for focusing and routing the infrared light through said first and second chambers, means for directing the infrared light alternately through said fractions, and means for measuring the infrared light and identifying the particles.

2. The apparatus of claim 1 wherein said means for separating the sample into said plurality of size fractions comprises a virtual impactor.

3. The apparatus of claim 1 wherein said filter means comprises a PTFE filter.

4. The apparatus of claim 1 wherein said means for impacting said fine particles against said internal reflection element comprises an impactor having opposing nozzles which direct said fraction against opposing sides of said element.

5. The apparatus of claim 1 wherein said first sample comprises coarse particles having an aerodynamic diameter of about 1 to 10 micrometers, and said second sample comprises fine particles having an aerodynamic diameter of about 0.3 to 1 micrometers and ultrafine particles having an aerodynamic diameter of less than about 0.3 micrometers.

6. The apparatus of claim 5 comprising means for collecting said ultrafine particles in second filter means, said ultrafine collecting means having a second sealed chamber and said second filter means being located inside said second chamber, and means for analyzing said ultrafine particles through infrared spectrophotometry in essentially real time, without removing said second filter means from said ultrafine collecting means.

7. A method of analyzing a sample from a gaseous environment, the sample having gaseous elements and suspended particles, comprising the steps of separating the sample into a plurality of fractions having different size particles, capturing particles in a first of said fractions in filter means which collect said first fraction, capturing particles in a second of said fractions against an internal reflection element to which said second fraction particles adhere, and analyzing said fractions with infrared spectrophotometry in essentially real time by alternating the positions of movable mirrors to direct infrared light emitted from a spectrophotometer alternately through said particle fractions.

8. Apparatus for analyzing a sample from an aerosol environment, the sample having gaseous elements with suspended particles, comprising, means for separating the sample into a plurality of size fractions, means for collecting a first fraction in filter means, said collecting means having a first sealed chamber and said filter means being located inside said first chamber, means for impacting a second fraction against an internal reflection element to which said second fraction adheres, said impacting means having a second sealed chamber and said internal reflection element being located inside said second chamber, and means for analyzing said fractions through infrared spectrophotometry in essentially real time, without removing said filter means from said first chamber, or said internal reflection element from said second chamber, said analyzing means including a plurality of movable mirrors which alternately direct infrared light through said particle fractions, and means for moving said mirrors, whereby said particle size fractions are analyzed alternately in essentially real time.

9. Apparatus for analyzing a sample from a aerosol environment, the sample having gaseous elements with suspended particles, comprising, means for separating the sample into a plurality of fractions each having selected particle sizes, a plurality of means for collecting a first selection of fractions in filter means, each fraction being collected in a respective filter means, each collecting means having a first sealed chamber, and each filter means being located inside a respective first chamber, a plurality of means for impacting a second selection of fractions against an internal reflection element to which said second selection of fractions adhere, each impacting means having a second sealed chamber and said internal reflection element being located inside a respective second chamber, and means for analyzing said fractions through infrared spectrophotometry in essentially real time, without removing said filter means from said first chambers, or said internal reflection element from said second chambers, said analyzing means including means for emitting infrared light, means for focusing and routing the infrared light through said first and second chambers, means for directing the infrared light alternately through said fractions, and means for measuring the infrared light and identifying the particles.

* * * * *